United States Patent [19]

Michelson

[11] Patent Number: 4,478,596
[45] Date of Patent: Oct. 23, 1984

[54] DELIVERY SYSTEM FOR PHYSIOLOGICALLY ACTIVE AGENTS

[76] Inventor: Paul E. Michelson, 2280 Calle Tiara, La Jolla, Calif. 92037

[21] Appl. No.: 444,376

[22] Filed: Nov. 26, 1982

[51] Int. Cl.³ .............................................. A61M 5/00
[52] U.S. Cl. .................................... 604/890; 604/893
[58] Field of Search ............................... 604/890–900; 424/18–25; 128/155, 156, 127–132

[56] References Cited

U.S. PATENT DOCUMENTS

| 3,426,754 | 2/1969 | Bierenhaum et al. |
| 3,832,458 | 8/1974 | Merrill |
| 3,967,618 | 7/1976 | Zaffaroni ............................ 604/892 |
| 4,077,407 | 3/1978 | Theeuwes |
| 4,265,874 | 5/1981 | Bonsen et al. |
| 4,298,003 | 11/1981 | Theeuwes |
| 4,309,996 | 1/1982 | Theeuwes |
| 4,314,557 | 2/1982 | Chandrasekaran |
| 4,322,398 | 3/1982 | Reiner et al. |

FOREIGN PATENT DOCUMENTS 990164 6/1976 Canada ................................ 604/893

OTHER PUBLICATIONS

*Remington's Pharmaceutical Sciences*, 16th Edition, Arthur Osol, Editor, Mack Publishing Co., 1980, pp. 182–193, "Complexation", Chapter 14, by Gennaro.
*Physical Pharmacy*, 2d Edition, Martin et al., Lea & Febiger, 1969, pp. 325–352, "Complexation", Chapter 13.

*Primary Examiner*—Benjamin R. Padgett
*Assistant Examiner*—T. J. Wallen
*Attorney, Agent, or Firm*—Spencer & Frank

[57] ABSTRACT

A system for the controlled delivery of a physiologically active agent to a fluid environment having a semipermeable sheath with a plurality of pores, the sheath being imperforate except for the plurality of pores and defining a fully enclosed cavity for holding a physiologically active agent. A physiologically active agent is contained in the fully enclosed cavity for delivery to a fluid environment, with the plurality of pores being of a size to permit both the flow of fluid from the fluid environment through the semipermeable sheath into the cavity and the flow of fluid and physiologically active agent in solution out of the cavity into the fluid environment whereby the physiologically active agent is delivered from the semipermeable sheath exclusively through the plurality of pores.

9 Claims, 3 Drawing Figures

DELIVERY SYSTEM FOR PHYSIOLOGICALLY ACTIVE AGENTS

BACKGROUND OF THE INVENTION

The present invention relates generally to an improved system for the delivery of physiologically active agents and, more particularly, to an improved delivery system for the timed release of physiologically active agents.

In recent years numerous devices have been devised which utilize osmotic flow to assist in the delivery of physiologically active agents. For example, both U.S. Pat. No. 4,265,874 to Bosen et al and U.S. Pat. No. 4,298,003 to Theeuwes et al disclose methods and devices for the delivery of a drug where, as a result of osmotic flow, fluid passes through a semipermeable membrane and forces an insoluble drug or a solution of a soluble drug out of the device through an enlarged opening or passageway. The membrane of these devices allows the flux of water only, not the drug. The drug is forced out, under the influence of osmosis, through the enlarged opening or passageway which is separately drilled in the devices and whose size is orders of magnitude larger than the pores of the membrane. U.S. Pat. No. 3,832,458 reveals a device in which a silicon polymer wall is utilized to vary permeability to an internal active agent. The permeability is adjusted by fabricating the wall with varying amounts of N-vinyl-pyrrolidone. While this device represents an improved delivery technique, it has a significant disadvantage in that it represents a "first order" delivery system in which the driving force of drug delivered to the outside is the result of the internal concentration of drug alone. Thus the drug will be delivered at an initial rapid rate followed by a significantly lower rate until the active agent is expended. U.S. Pat. No. 4,309,996 by Theeuwes discloses a somewhat different mechanism for delivery of drugs whereby a separate compartment filled by a net osmotic inflow is utilized to expand against a flexible internal partition which forces active agent out of a second compartment through a microporous structure thus attempting to approximate a steady delivery rate.

In summary, while the prior art devices have resulted in improved delivery techniques, they are either somewhat complex, adding to the cost of the devices, or unable to control the precise drug delivery rate. It is therefore advantageous to provide a system which is flexible in that there are numerous variables which can be modified to control the delivery rate of the drug.

SUMMARY OF THE INVENTION

It is an object of the present invention to provide a new and improved system for delivering physiologically active agents.

It is a further object of the present invention to provide a new and improved system for the delivery of a physiologically active agent which is less complex than prior art devices.

It is an additional object of the present invention to provide a new and improved system for the delivery of physiologically active agents which permits more control and flexibility in the amount and rate of delivery of active agents than prior art devices.

It is another object of the present invention to provide a new and improved system for the delivery of physiologically active agents which utilizes the pores of a semipermeable membrane to deliver the active agent to a surrounding fluid environment.

Additional objects and advantages of the present invention will be set forth in part in the description which follows and in part will be obvious from the description or can be learned by practice of the invention. The objects and advantages are achieved by means of the processes, instrumentalities and combinations particularly pointed out in the appended claims.

To achieve the foregoing objects and in accordance with its purpose, the present invention provides a system for the controlled delivery of a physiologically active agent to a fluid environment comprising a semipermeable sheath having a plurality of pores and being imperforate except for the plurality of pores and defining a fully enclosed cavity for holding a physiologically active agent. A physiologically active agent is contained in the fully enclosed cavity for delivery to a fluid environment, said plurality of pores being sized to permit both the flow of fluid from the fluid environment through the semipermeable sheath into the cavity and the flow of fluid and physiologically active agent in solution out of the cavity to the fluid environment whereby said physiologically active agent is delivered from said semipermeable sheath exclusively through said plurality of pores.

DESCRIPTION OF THE PREFERRED EMBODIMENTS

Figure 1:
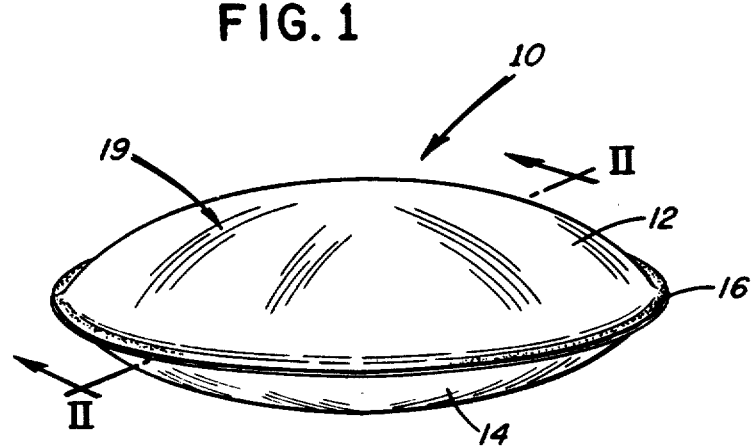
FIG. 1 is a perspective view of a system according to the invention.

In accordance with the invention, as shown in FIG. 1, a device 10, which is generally of circular configuration, but whose shape may vary as appropriate for differing sites of application, consists of a semipermeable sheath 19 which is made of two thin sheets 12 and 14. The thin sheets 12 and 14 are bound along their respective edges to form a sheath with an outside edge 16. As will be apparent hereafter, the delivery system according to the invention, is intended to be used in a fluid environment with sufficient fluid present to enable the system to operate as intended. Furthermore, as with the prior art devices, the system according to the invention, is particularly suitable for the delivery of active agents to animals and may be located with respect to the animal to be treated by positioning or implanting the system in a variety of locations such as the animal's rectum or gastrointestinal tract, etc.

Figure 2:
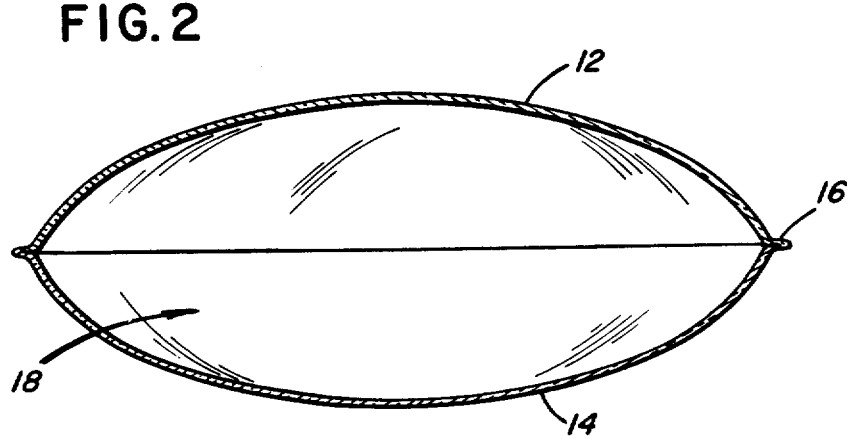
FIG. 2 is a sectional view along the section line I—I in FIG. 1.

As can be seen in FIG. 2, thin sheets 12 and 14 define a cavity 18 which is intended to contain a physiologically active agent. Thin sheets 12 and 14 are provided with a plurality of pores in order to be semipermeable and permit the passage of fluid therethrough. The semipermeable thin sheets 12 and 14, when joined to form edge 16, result in a semipermeable sheath.

The present invention utilizes the principle of osmotic flow which results from a difference in molecular concentration being present across a semipermeable membrane.

According to the invention, cavity 18 will contain at least a physiologically active agent which will go into solution with fluid which will enter cavity 18. The physiologically active agent may or may not be fully soluble as long as it can be delivered from device 10 at a suitable and predictable rate. As will be described in more detail hereinafter, in a preferred embodiment of the invention, a macromolecule may also be present in cavity 18. The term macromolecule is intended to mean a large molecule such as a protein, carbohydrate, rubber or other natural or synthetic high polymer.

The presence of an active agent in cavity 18 results in a net molecular concentration gradient being set up between the cavity 18 and the fluid environment in which the lens is used. This net molecular concentration gradient will result in flow of fluid from the fluid environment through the semipermeable sheath into cavity 18. This flow of fluid, generally referred to as osmotic flow, results from the net higher molecular concentration or net higher osmotic pressure which is present in cavity 18 due to the presence of a physiologically active agent alone or the physiologically active agent and the macromolecule. That is, the body of fluid inside the semipermeable sheath is hypertonic with respect to the fluid outside of the semipermeable sheath, i.e. the fluid inside the semipermeable sheath has a higher osmotic pressure than the fluid outside the semipermeable sheath. See applicant's copending Application "Fluid Lens" Ser. No. 432,409, filed Sept. 30, 1982.

When measured at any given instance, the osmotic pressure inside cavity 18 will be higher than that of the fluid surrounding the device and, therefore, there will be a net inward flow of fluid. However, over a period of time fluid continuously enters and leaves cavity 18 which results in a dispersion of the active agent from cavity 18. While there will be continuing "steady-state" flux of fluid between the environment and internal fluid of the device, the net inflow of fluid volume will occur in the initial states under the influence of osmosis until the osmotic pressure and fluid inflow result in the device achieving its natural premolded configuration. The burst strength of the encapsulating polymer film and its seal exceed the maximum achievable osmotic pressure by at least several orders of magnitude. The continuing steady-state flux of fluid across the walls of the device will result in the dispersion of any active agent whose molecular size is such as to allow passage through the preselected pore diameter of the membrane wall.

The osmotic flow which results due to molecular concentration differences is independent for each molecule involved. For example, in the above example if the macromolecule, designated A, and another molecule, designated B, were added to cavity 18, and went into solution and became part of the body liquid 19, molecule B would set up a concentration gradient across the semipermeable sheath independent of the gradient present as a result of macromolecule A. The osmotic flow resulting from the presence of molecule B would be independent of the osmotic flow resulting from the presence of macromolecule A.

In a preferred embodiment of the invention a macromolecule would be complexed with the physiological agent and the macromolecule selected such that it would be larger than the pores of the semipermeable sheath, yet the complex would decay over a period of time thereby allowing the active agent to slowly disperse from the semipermeable sheath.

The macromolecule, according to the invention, may be selected from any class of compounds with molecular weight and configuration sufficiently large to be excluded passage by the desired pore size. Generally suitable are the dextrans, amylopectins (hydroxyethylstarch), polyvinylpyrrolidone, polyethylene glycol, albumin and various other soluble polymers and/or proteins. Alternatively, emulsions with droplets containing active agent can be utilized as well. Microemulsions with droplets of a diameter range 0.01 to 0.1 microns are transparent and optically clear and thus, preferable for optical systems whereas macroemulsions with droplet of size 0.1 to 1 or 2 micrometers may be satisfactory in other uses.

The active agents suitable for use in connection with the present invention include for examples: oxygen, preferentially bound to fluorocarbons; salicylates, catechols, halogens, barbiturates or other compounds complexed to a macromolecule such as polyethylene glycols; antibiotics such as chloramphenicol, sulfa or other medications complexed with a macromolecule such as polyvinylpyrrolidone; antiepileptic medications such as phenytoin complexed to albumin; antihistamines, quinine, procaine or other compounds complexed to a macromolecule such as sodium carboxymethylcellulose; salicylates complexed to the antibiotics oxytetracycline or tetracycline or other compounds complexed to a macromolecule such as salicylates or other macromolecules could be utilized such as caffeine or albumin. The above identified complexes have well known association constants. See generally *Remington's Pharmaceutical Sciences*, 16th Edition, Arthur Osol, Editor, Mack Publishing Co. 1980, pp. 182–193 and *Physical Pharmacy*, 2d Edition, Martin et al, Lea & Febiger, 1969, pp. 325–352.

A given delivery rate of active agent and/or complexing molecule can be achieved through selection of appropriate membrane pore size, density, environmental conditions and binding molecule. Active agent and binding molecule form a molecular complex with an affinity for each other which can be expressed as an association constant, an easily determined quantity related to concentration and physicochemical environment. This constant is directly proportional to the concentration of the complex and inversely proportional to the product of the concentrations of active agent uncomplexed and binding molecule uncomplexed. It can thus be seen that if a nondiffusable binding molecule is chosen, the further dampening of a potentially rapid or exponential rate of delivery of active agent can be achieved. In simple form, if the association constant is represented as K, the molar concentration of the drug as (D), the binding molecule concentration as (B), and the bound complex as (B-D), the following represents the relationship described: $K = (B\text{-}D)/(B)(D)$.

The thickness of the semipermeable sheet material, utilized in connection with the invention, will depend on a number of factors and is directly related to the intended use of the delivery system. Generally, the membrane thickness will range from 5–10 micrometers, depending upon the material used and the intended configuration and concentration gradient. Sheet material could be selected from cellulose acetate, cellulose acetate butyrate, cellulose triacetate, poly-1, 4 butylene terephthalate (such as MYLAR ®), polymethylmethacrylate, polypropylene (such as CRYOVAC ®), polystyrene, polyvinyl acetate, polyvinyl chloride, polyvinyl fluoride, polyvinylidene chloride (such as SARAN ®), polycarbonate or silicon-polycarbonate copolymers (such as NUCLEPORE ®) and others.

The transparent sheets can be made porous in a variety of ways. For example, the technique of nuclear track etching can be used, in which the polymer films are exposed to radioactive decay particles and products and then treated chemically to "etch" permanently the tracks of the particles through the film, thus creating pores of a size and density determined by the exposure time and etching process. The particle dose determines the hole density while the pore diameter is a function of etching time. The specific particles, dose, etchants, and other conditions to achieve desired pore sizes and density for the aforementioned polymer films are well known in the prior art. See *Nuclear Tracks in Solids, Principals and Applications,* R.L. Fleischer et al, University of California Press, 1975. For example, polycarbonate filters (such as NUCLEPORE®) are produced by exposure to $U^{235}$ followed by sodium hydroxide etching. Polyvinylidene chloride (such as SARAN®) can be made microporous by exposure to fission fragments of Californium 252 followed by etching with potassium permanganate at 55 degrees Centigrade. As an alternative to nuclear tracking etching, the newer advanced lasers such as frequency-doubled Neodymium-YAG, Excimer, tunable dye or other lasers may be used to produce pores of the desired size and density.

Pores may also be created by forming membranes as integrated sheets of polymer containing "pore-formers," molecules which subsequently can be leached or dissolved out, leaving a predictable pore size. The leaching or dissolution can be accomplished prior to use or so selected to occur in the environment of use. For example, certain polymer films made of various polycarbonates, polyamides, or polyesters can include such pore formers as lithium carbonate, calcium phosphate, various polysaccharides, such as mannitol, CARBOWAX®, etc. These above processes, and others for creating microporous membranes, are noted in the prior art literature and are compiled in such works as *Synthetic Polymer Membranes* by R. E. Kesting, McGraw-Hill, Inc., 1971.

The pore size will preferably range between 50 Angstroms diameter to 1,000 Angstroms; however, it may be possible to have pore sizes smaller than 50 Angstroms, if desired. The pore size is selected depending on the molecular weight and configuration of the macromolecule. For example, a pore size of approximately 60 Angstroms will exclude a molecule having a molecular weight of about 10,000. A 100 Angstrom pore size will exclude a molecule having a 100,000 molecular weight. The exact three dimensional configuration of the molecules may, of course, produce exceptions. Pore density would be on the order of $10^5$ to $10^{10}$ per square cm; however, depending on the application of the device, pore densities less than $10^5$ per square cm may be used.

The thin sheets 12 and 14 may be joined at their respective edges to form edge 16 in a variety of ways. Various heat and impulse sealers can be used with variations in temperatures, frequency, and times allowing for substantial flexibility depending upon the particular polymer. Various one-part and two-part compatible adhesive bonding systems such as EASTMAN 910®, EPON 828® and 3M CONTACT CEMENT® could also be used. In addition, some materials are suitable for bonding without using conventional bonding methods. For example vinylidene chloride may be sealed to itself while in the so-called "supercooled" state to form a strong bond without conventional dielectric heat or adhesive methods.

Osmotic pressures generated in cavity 18 obviously will be significantly less than the burst strength of the semipermeable membranes. For example, the pressure generated by the macromolecule will be in the order of less than 0.34 atmosphere (5 pounds per square inch), while, for example, the burst strength of vinylidene chloride 1 mil thick is 30 pounds per square inch.

The following specific examples of delivery systems, in accordance with the invention, are set forth as illustrative only, and should not in any way limit the scope and purpose of the present invention.

A delivery system for the drug phenytoin, is constructed by forming a sheath made from planar sheets of polycarbonate membrane, with pore size of 0.015 micrometers, porosity $12 \times 10^8 / cm^2$ and thickness 6 micrometers. The polycarbonate membrane is heated to 220 degrees centigrade, and molded by vacuum or pressure to a spherical cap of 6.0 mm diameter with radius of curvature, 6.4 mm. A ½ mm wide planar circumferential cuff is left about each empty spherical cap. Then, 25µ g of phenytoin, along with 100µg of albumin are placed into one cap after which the opposing cap is utilized as a cover and the circumferential cuff of ½ mm is sealed together at 230–275 degrees centigrade. This creates an envelope of potential volume 11.92 cu mm. Placed in the fluid environment of use, the delivery system will fill to its normal volume.

Figure 3:
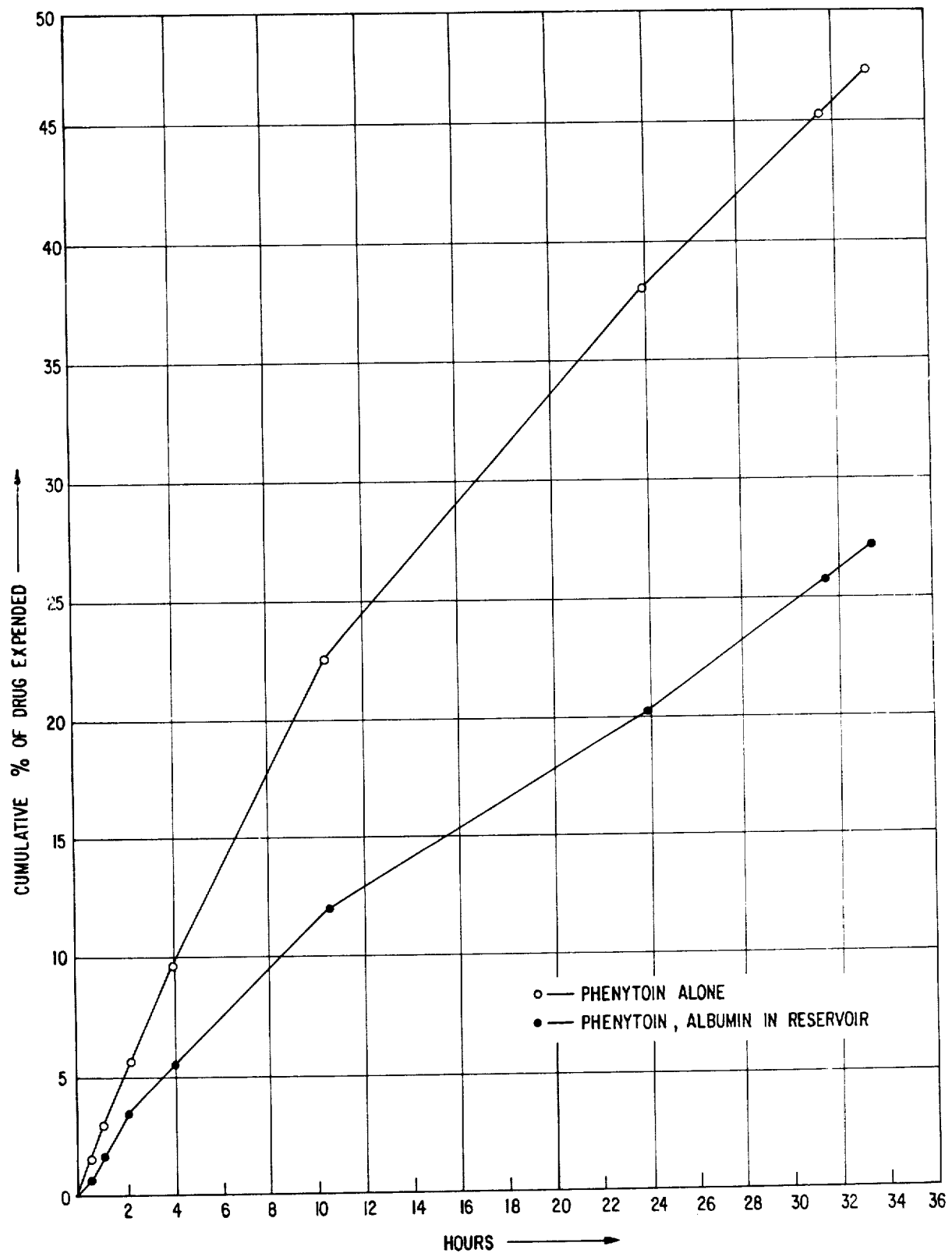
FIG. 3 is a plot of the drug delivery rates of systems according to the invention.

FIG. 3 is a plot of the delivery rate of systems according to the invention comparing the delivery rate of a system containing phenytoin-albumin complex with the delivery rate of a system containing phenytoin alone. In the first half-hour the system utilizing the drug phenytoin-albumin complex shows that 0.74% of its drug content by weight will have been expended and after one hour a total of 1.7% will have been expended, and so on for the following intervals: 2 hrs, 3.4%; 4 hrs, 5.4%; 10 ½ hrs, 12%; 24 hrs, 20.2%; 33 ½ hrs, 27.2%.

By contrast, an identical device containing only phenytoin without albumin will deliver at the indentical time intervals as noted above, the following percentages of the initial amount of drug placed in the device: ½ hr, 1.47%; 1 hr, 2.97%; 2 hrs, 5.7%; 4 hrs, 9.6%; 10 ½ hrs, 22.4%; 24 hrs, 38%; 33 ½ hrs, 47.2%.

It will be understood that the above description of the present invention is susceptible to various modifications, changes and adaptations, and the same are intended to be comprehended within the meaning and range of equivalents of the appended claims.

What is claimed is:

1. A system for the controlled delivery of a physiologically active agent to a fluid environment comprising:

a semipermeable sheath defining a fully enclosed cavity and being imperforate except for a plurality of pores for permitting the flow of fluid from the fluid environment into said cavity; and a quanitity of a molecular complex positioned in said cavity, said molecular complex comprising a macromolecule that is nondiffusable with respect to said sheath and a physiologically active agent complexed to said macromolecule, said physiologically active agent being capable of dissociating from said macromolecule over time and going into solution with the fluid in said cavity, and said pores having a larger size in relation to said physiologically active agent and said sheath being so constructed as to permit unimpeded passage of said physiologically active agent through said pores out of said cavity, wherein the concentration of said physiologically active agent within said cavity is controlled by the equilibrium between said molecular complex and said physiologically active agent within said cavity and said physiologically active agent is deliverable by said system to the fluid environment exclusively through said plurality of pores.

2. The system of claim 1 wherein said sheath has a thickness of less than 50 microns.

3. The system of claim 1 wherein the diameter of said pores is less than 1,000 Angstroms.

4. The system of claim 1 wherein said sheet has a pore density between 100 and $10^{10}$ pores per square cm.

5. The system of claim 1 wherein said pores are sufficiently small to prevent the passage therethrough of said macromolecule.

6. The system of claim 1 wherein said sheath is transparent and said macromolecule is photostable.

7. The system of claim 1 wherein said macromolecule is inert.

8. The system of claim 1 wherein said macromolecule is selected from a group consisting of protein, cellulose, carbohydrate, rubber or high polymer.

9. A drug delivery system for immersion in a physiological fluid comprising:

a semipermeable sheath defining a fully enclosed cavity and having a plurality of pores for permitting the physiological fluid to flow into and out of said cavity, said sheath being imperforate except for said pores; and a quanity of a molecular complex disposed in said cavity, said molecular complex comprising a macromolecule and a drug complexed to said macromolecule which, overtime, dissociates from said macromolecule to create a free drug and an uncomplexed macromolecule both of which go into solution with the fluid in said cavity, said uncomplexed macromolecule being larger than the pores in said sheath and thereby prevented from leaving said said cavity and said pores being larger in size in relation to said free drug and said sheath being so contructed as to premit said free drug to pass unimpeded through said pores for delivery to the physiological fluid surrounding said sheath;

wherein the fluid flows into the cavity under the influence of osmotic pressure and the concentration of free drug within said cavity is controlled by the equilibrium between said molecular complex and said free drug within said cavity.

* * * * *